(12) United States Patent
Buechler et al.

(10) Patent No.: US 7,588,908 B2
(45) Date of Patent: Sep. 15, 2009

(54) COMPOSITIONS AND METHODS FOR INHIBITING LIGHT-INDUCED INACTIVATION OF BIOLOGICAL REAGENTS

(75) Inventors: Kenneth F. Buechler, San Diego, CA (US); Paul H. McPherson, Encinitas, CA (US); Alfred R. Sundquist, San Diego, CA (US)

(73) Assignee: Biosite, Inc., Waltham, MA (US)

( * ) Notice: Subject to any disclaimer, the term of this patent is extended or adjusted under 35 U.S.C. 154(b) by 1226 days.

(21) Appl. No.: 10/338,182

(22) Filed: Jan. 7, 2003

(65) Prior Publication Data
US 2003/0129642 A1    Jul. 10, 2003

(51) Int. Cl.
G01N 33/00 (2006.01)
G01N 33/543 (2006.01)

(52) U.S. Cl. .................. 435/7.92; 436/518
(58) Field of Classification Search .......... 435/69.7, 435/7.92; 530/402; 436/176, 183, 800, 546, 436/56, 86, 518
See application file for complete search history.

(56) References Cited

U.S. PATENT DOCUMENTS

| | | | |
|---|---|---|---|
| 4,283,382 A | | 8/1981 | Frank et al. |
| 4,351,760 A | | 9/1982 | Khanna et al. |
| 4,420,568 A | | 12/1983 | Wang et al. |
| 4,868,132 A | | 9/1989 | Byrnes et al. |
| 4,876,190 A | | 10/1989 | Recktenwald |
| 5,075,215 A | | 12/1991 | Dreyer |
| 5,230,836 A | * | 7/1993 | Todd, Jr. ............. 252/407 |
| 5,434,088 A | * | 7/1995 | Ikeda et al. ........... 436/525 |
| 5,709,994 A | * | 1/1998 | Pease et al. ........... 435/4 |
| 5,747,334 A | * | 5/1998 | Kay et al. ............. 435/320.1 |
| 6,251,687 B1 | * | 6/2001 | Buechler et al. ........ 436/518 |

FOREIGN PATENT DOCUMENTS

| | | |
|---|---|---|
| EP | 0 442 372 A | 8/1991 |
| WO | WO 91/18006 A | 11/1991 |
| WO | WO 92/18868 A | 10/1992 |
| WO | WO 95/08772 * | 3/1995 |
| WO | WO 95/08772 A | 3/1995 |
| WO | WO 96/17626 A | 6/1996 |
| WO | WO 96/41174 A | 12/1996 |

OTHER PUBLICATIONS

Bystryak et al. "A homogeneous immunofluorescence assay based on dye-sensitized photobleaching." Analytical Biochemistry, 225m 127-134, 1995.*
Andley et al. "Accessibilities of the sulfhydryl groups of native and photooxidized lens crystallins: A fluorescence lifetime and quenching study." Biochemistry, 1988, 27, 810-820.*
Misra et al. "Vasoactive intestinal peptide, a singlet oxygen quencher." The Journal of Biological Chemistry, 265, 26, 15371-15374, Sep. 15, 1990.*
Shimada et al., Jpurnal of Immunological Methods, 1991, vol. 136, No. 2, pp. 159-168.*
Laranjinha et al. (Archives of Biochemistry and Biophysics, vol. 297, No. 1, Aug. 15, 1992, pp. 147-154).*
Bystryak et al. (Anal. Biochem. 225: 127-134, 1995).*
Frimer, A., Ph.D., "Singlet $O_2$" *Polymers and Biomolecules*, IV:91-143 (1985).
Rosenthal, I., et al., "Role of Oxygen in the Phototoxicity of Phthalocyanines", *Int. J. Radiat. Biol.*, 67(1):85-91 (1995).
Spikes, J., et al., "Rapid Communication. Zinc Tetrasulphophtlhalocyanine as Photodynamic Sensitizer for Biomolecules", *Int. J. Radiat. Biol.*, 50(1):41-45 (1986).
Ullman, E., et al., "Luminescent Oxygen Channeling Assay (LOCI™): Sensitive, Broadly Applicable Homogenous Immunoassay Method", *Clinical Chemistry*, 42(9):1518-1526 (1996).
van Lier, J., et al., "The Chemistry, Photophysics and Photosensitizing Properties of Phthalocyanines", *Ciba Foundation Symposium*, 146:17-26 (1989).
Wohrle, D., et al., "Phthalocyanines and Related Macrocycles for Multi-electron Transfer in Catalysis, Photochemistry and Photoelectrochemistry", *Polymers for Advanced Technologies*, 6(3):118-130 (1995).

* cited by examiner

*Primary Examiner*—Lisa V Cook
(74) *Attorney, Agent, or Firm*—Anavelys Ortiz-Suarez; Wilson Sonsini Goodrich & Rosati

(57) ABSTRACT

Disclosed is a fluorescent conjugate comprising a biological reagent, a fluorescent molecule, and a means for impeding phototoxic degradation of the biological reagent. The impeding means can be a cross-linking substance having a long molecular distance, whereby the cross-linking substance links the fluorescent molecule and the biological reagent; a quencher of singlet oxygen; a quencher of a free radical; or a combination thereof. Also disclosed is a solution comprising a fluorescent conjugate of a biological reagent and a fluorescent molecule together with an oxygen depleting system.

17 Claims, No Drawings

US 7,588,908 B2

COMPOSITIONS AND METHODS FOR INHIBITING LIGHT-INDUCED INACTIVATION OF BIOLOGICAL REAGENTS

This application claims the priority of U.S. application Ser. No. 08/837,309, entitled "Novel Compositions and Methods For Inhibiting Light-Induced Inactivation Of Biological Reagents," filed Apr. 9, 1997, now issued as U.S. Pat. No. 6,544,797, which is incorporated by reference herein in its entirety.

FIELD OF THE INVENTION

This invention relates to the stabilization of fluorescent conjugates, in particular to stabilization of biological reagents, such as proteins, peptides, ligand analogues and nucleic acids, conjugated to a fluorescent molecule or to a fluorescent particle.

BACKGROUND ART

In order to determine the presence or concentration of target ligands or analytes in a fluid, immunoassays utilize binding proteins, such as antibodies, to specifically bind to target ligands or analytes. Commonly, a signal is generated from the immunoassay to provide a detectable or sensible result. A class of useful signal generators are fluorescent molecules because of their high specific activity.

Fluorescent molecules have been utilized in immunoassays as signal generators in several ways. For example, enzymes can catalyze the production of fluorescent dyes from a substrate, such that the amount of fluorescent dye generated is related to the presence or amount of analyte or target ligand in a sample; such enzymes can be conjugated to antibodies or ligand analogues. Fluorescent dyes can also be conjugated to antibodies or ligand analogues, and the amount of fluorescent signal is measured as a result of the assay process to define the analyte presence or amount.

An objective with immunoassays is to make them more sensitive, so that a lower concentration of analyte can be measured. To increase sensitivity, one can conjugate a biological reagent to a fluorescent particle. As used herein, "fluorescent particles" can be formed of a synthetic material such as latex, can comprise a natural material such as liposomes, or combinations of natural and synthetic materials. In the preparation of the fluorescent particles, the fluorescent dyes or enzymes are generally imbibed into and/or adsorbed onto the particles, using mixed organic and aqueous solutions. The fluorescent dyes or enzymes incorporated into particles are usually water insoluble, whereas the dyes or enzymes conjugated directly to biological reagents are generally water soluble.

One can conjugate, for example, a biological reagent to a fluorescent particle that contains many fluorescent molecules or enzymes capable of converting a substrate into a fluorescent product. In the case of conjugating an antibody to a fluorescent particle, the analyte that is bound by the antibody conjugated to the fluorescent particle containing many fluorescent molecules is thus associated with a larger signal as compared with binding an antibody that is conjugated with a single fluorescent molecule or enzyme.

Examples of immunoassays that incorporate fluorescent dyes or enzymes are numerous and some are described in U.S. Pat. Nos. 4,283,382; 4,351,760; 4,420,568; 4,868,132; 4,876,190; 5,075,215; and, E.P.O. Application Number PCT/US87/03226.

Immunoassays are characterized as either competitive or non-competitive. Competitive immunoassays generally operate by a competition between a ligand analogue signal generator complex and a ligand (i.e., the analyte) for binding to a limited amount of antibody. Competitive immunoassays can also function by a competition between a protein or an antibody signal generator conjugate and an analyte which is a protein or an antibody, respectively, for binding to a limited amount of ligand. Non-competitive immunoassays generally function by having two different antibodies bind the analyte at different epitopes, one antibody conjugated to the signal generator and the other antibody in solution or bound to a solid phase in order to facilitate separation of unbound signal generator from the bound signal generator.

The antibody concentration in an immunoassay generally dictates the kinetics of the immunoassay, as well as the fraction of analyte bound to the antibody. In general, to accelerate the binding of an analyte to an antibody so that the reaction achieves a desired reaction rate or equilibrium in a desired time, the highest antibody concentration that is feasible is used in the assay; this is particularly true for non-competitive immunoassays. Thus, a high antibody concentration is often employed in fluorescent assays. Generally a high antibody concentration is also associated with a high fluorescent dye concentration, since each make up the antibody:particle conjugate or the antibody:dye conjugate.

Thus, for immunoassays, fluorescent particles are often used to obtain a more sensitive measure of analyte concentration. The quantity of a fluorescent molecule that needs to be associated with a complex of an analyte and a fluorescent conjugate is generally determined based on the sensitivity requirements of the assay. Thus, for sensitive assays, the amount of fluorescent dye or enzyme associated with the analyte in the assay process, is maximized. In such a case, the local concentration of fluorescent molecules is very high in the immediate vicinity of the biological reagent because they are in close proximity to each other.

Nucleic acid assays also utilize fluorescent sinal generators. Signal generators associated with nucleic acids are used in assays to measure nucleic acids complementary with the nucleic acid associated with a signal generator. In order to optimize the hybridization kinetics with the target nucleic acid and also to achieve the most sensitive assay, these nucleic acids are also at a high local concentration in the vicinity of fluorescent molecules. To create a nucleic acid conjugate, a signal development element is conjugated to a nucleic acid sequence. The signal development element can be a fluorescent particle or a fluorescent molecule.

Previously, however, a problem was encountered with fluorescent conjugates for use in assays. Often, fluorescent conjugates were not stable. The reactivity of such conjugates was found to decay over time, such that the function or properties of a biological reagent in a fluorescent conjugate would change with time. For example, the binding affinity of an antibody linked to a fluorescent signal would often decrease with time. The mechanism(s) for this degradation of the properties of biological reagents in fluorescent conjugates was not known. It was presumed, however, that the degradation occurred consequent to the release or uncoupling of the biological reagent from the fluorescent molecule.

DISCLOSURE OF THE INVENTION

For the first time in the art, the mechanisms leading to the degradation of biological reagents in fluorescent conjugates has been identified. Accordingly, compositions and methods are provided to modulate this degradation, both in fluorescent conjugates and in the reagents used to synthesize the fluorescent conjugates. The effectiveness of fluorescent conjugates for use in assays is enhanced pursuant to the present invention.

Thus, disclosed is a fluorescent conjugate comprising a biological reagent, a fluorescent molecule, and a means for impeding phototoxic degradation of the biological reagent. The impeding means can comprise a cross-linking substance having a long molecular distance, whereby the cross-linking substance links the fluorescent molecule and the biological reagent; a protein; a quencher of singlet oxygen; a quencher of a free radical; a system for depleting oxygen; or a combination thereof.

The conjugate can comprise that the fluorescent molecule is directly linked to the biological reagent. The conjugate can further comprise a particle which comprises a fluorescent molecule; the particle can comprise a natural material or a synthetic material. For example, the particle can comprise a natural material which is alumina, silica, or, a liposome. The particle can further comprise an oxygen depleting system.

Disclosed is a solution comprising a fluorescent conjugate and an oxygen depleting system. For an embodiment of the fluorescent conjugate to be placed in a solution, the solution can comprise an means for impeding phototoxic degradation. The impeding means of the solution can comprise an antioxidant, a protein, an oxygen depleting system, or a combination thereof. The fluorescent conjugate of the solution can comprise a biological reagent, a fluorescent molecule, and a means for impeding phototoxic degradation of the biological reagent. The impeding means of the conjugate in the solution can comprise: a system to deplete oxygen; a cross-linking substance having a long molecular distance, whereby the cross-linking substance links the fluorescent molecule and the biological reagent; an antioxidant; a protein; or, a combination thereof.

Also disclosed is a fluorescent conjugate prepared by a process comprising steps of: providing a biological reagent; providing a fluorescent molecule; providing a heterofunctional linking reagent; chemically reacting the biological reagent, the fluorescent molecule, and the heterofunctional linking reagent, whereby the biological reagent becomes linked to the fluorescent molecule; and; associating an oxygen depleting system, a protein, an antioxidant, or a combination thereof, with the biological reagent or the fluorescent molecule prior to the reacting step; or, associating an oxygen depleting system, a protein, an antioxidant, or a combination thereof, with the linked biological reagent and fluorescent molecule following the reacting step. The heterofunctional linking reagent can be: a heterofunctional polyethylene glycol (PEG) derivative, a long chain form of succinimidyl-4-(N-maleimidomethyl)cyclohexane-1-carboxylate (SMCC), a long chain form of succinimidyl 3-(2-pyridyldithio)propionate (SPDP), or, a heterofunctional peptide derivative.

Disclosed is a method of use of an antioxidant, a protein, an oxygen depleting system, or a cross linking substance to impair the phototoxic degradation of a biological reagent in a fluorescent conjugate comprising the biological reagent and a fluorescent molecule, or to impair the phototoxic degradation of the material used to prepare a composition comprising a fluorescent molecule, the method occurring by combining an antioxidant, a protein, an oxygen depleting system, or a cross linking substance with the fluorescent conjugate, or with the material used to prepare a composition comprising a fluorescent molecule.

Also disclosed is a method to facilitate preparation of a stable fluorescent composition, where the composition comprises a fluorescent molecule which absorbs light and provides a fluorescent result upon exposure to light of a defined spectrum. The method comprises: providing an environment comprising diminished amounts of light from the defined spectrum, relative to a white light environment; providing the fluorescent molecule, or a material to prepare the composition; placing the fluorescent molecule or the material to prepare the composition into the provided environment. An embodiment of the method is disclosed which comprises: providing the fluorescent molecule; providing the material to prepare the composition; placing the fluorescent molecule into the provided environment; placing the material to prepare the composition into the provided environment; and, combining the fluorescent molecule and the material to prepare the composition; whereby phototoxic degradation of the material to prepare the composition is diminished upon completion of the method. When this embodiment of the method is performed, the combining step can occur before the step of placing the fluorescent molecule into the provided environment and before the step of placing the material to prepare the composition into the provided environment.

Definitions

Fluorescent molecule—As used herein, a fluorescent molecule is one that either emits light during the transition from an excited electronic state to a lower energy state, or is an enzyme or catalyst that is capable of acting on a substrate to yield a molecule that emits light during the transition from an excited electronic state to a lower energy state.

Fluorescent dyes—Fluorescent dyes are those that emit light during the transition from an excited electronic state to a lower energy state. The lower energy state is commonly referred to as the ground state. The excited state is attained by absorption of light at an appropriate wavelength. One pathway for relaxation of the excited state is the emission of light. Fluorescent dyes exhibit singlet-singlet emission of light.

Fluorescent particles—A particle which comprises one or more fluorescent molecules. A fluorescent particle can be formed of a synthetic material such as latex, can comprise a natural material such as liposomes, or can comprise a combination of natural and synthetic materials.

Ligand—A binding partner to a ligand receptor or to a complementary nucleic acid sequence.

Ligand analogue—A chemical derivative of a ligand. A ligand analogue may be attached either covalently or noncovalently to another species, for example, to a signal development element. Ligand analogue and ligand may be the same and both are capable of binding to ligand receptor.

Ligand Receptor—A receptor capable of binding ligand. Typically, a ligand receptor is an antibody or a complementary nucleic acid sequence, but may also be a ligand.

Signal Development Element—The element of the biological reagent conjugate that produces a detectable signal. The signal can be directly produced by the signal development element, or produced upon exposure of the signal development to a substrate.

Radical—A radical is an atom or a group of atoms that possess an unpaired electron. Radicals are also referred to as free radicals, diradicals and radical pairs.

Biological Reagent—A moiety, e.g., a protein, peptide, ligand analogue, or nucleic acid capable of being associated with a signal development element in a conjugate.

Fluorescent conjugates—A fluorescent conjugate comprises a biological reagent, e.g., a protein, peptide, ligand analogue or nucleic acid sequence, in association with a fluorescent molecule, a fluorescent particle, an enzyme, or a generator of fluorescent dyes. The association can be covalent or non-covalent.

The fluorescent molecules can be conjugated with natural or synthetic particles to form fluorescent particles. For example, a fluorescent molecule can be adsorbed to alumina or silica particles, or imbibed into latex particles or liposomes; the proteins, peptides, ligand analogues or nucleic acids can be adsorbed or covalently coupled to the particles to make the fluorescent conjugates. Alternatively, fluorescent molecules can be directly coupled to the proteins, peptides, ligand analogues or nucleic acids to form fluorescent conjugates. The direct coupling can be a covalent bond. The fluorescent molecules utilized for these latter conjugates are generally water soluble having a carboxylic acid, thiol, amine, maleimide, alkyl halide or N-hydroxy succinic ester moiety to facilitate coupling to the proteins, peptides, ligand analogues or nucleic acids.

Antioxidant—A substance such as a quencher which, when present in a system significantly delays or inhibits oxidation of the substrate.

Reactive species—Examples of reactive species are singlet oxygen, free radicals and excited triplet states.

Quencher—A substance which either through physical means, such as energy transfer, or through chemical means delays or inhibits the decomposition of another substance.

MODES FOR CARRYING OUT INVENTION

For the first time in the art, the mechanisms that lead to the degradation of biological reagents in fluorescent conjugates have been identified. It has been found that ambient white light leads to the generation of singlet oxygen or radicals which act on biological reagents. The studies that led to this finding are disclosed, as are compositions and methods to modulate this degradation. Pursuant to the present invention, the effectiveness of fluorescent conjugates for use in assays is enhanced.

Although the degradation of biological reagents in fluorescent systems had been note, the causative mechanism was unknown. Surprisingly, it was found that biological reagents such as antibodies, peptides and ligand analogues, as well as reagents used to synthesize the fluorescent conjugates, are degraded by a mechanism that is induced upon exposure of these materials to routine ambient conditions. The ambient conditions can constitute mere exposure to white light and oxygen.

Accordingly, this invention concerns the stabilization of proteins, peptides, ligand analogues and nucleic acids that are comprised in fluorescent conjugates, as well as stabilization of the materials to make fluorescent conjugates.

Mechanism(s) of Degradation of Biological Reagents

The inactivation of antibody binding activity in immunoassays or inactivation of nucleic acid hybridization assays by singlet oxygen or radicals has not been previously described. Previously, only the inactivation of lysozyme and the oxidation of amino acids have been described (*Singlet Oxygen*, 1985, Vol. IV, p. 91-143, ed. A. A. Frimer, CRC Press, Boca Raton, Fla.; *Int. J. Radiat. Biol.* (1986) 50:41-45); however, these descriptions are related to fluorescent dyes that are not conjugated to proteins, peptides, ligand analogues and nucleic acids; unlike the present invention, these dyes and biological reagents were freely soluble in aqueous solutions.

Furthermore, it has been noted that phthalocyanines can also initiate phototoxicity by an electron transfer mechanism (Type 1) in which the fluorescent dye, in an excited triplet state, can undergo reactions with neighboring molecules by an electron or hydrogen transfer process. The production of singlet oxygen (Type II) by the excitation of fluorescent dyes has been utilized for photodynamic therapy (*Polym. Adv. Technol.* (1995) 6:118-130; *Int. J. Radiat. Biol.* (1995) 67:85-91; *Ciba Foundation Symposium* (1989) 146:17-26) and in immunoassays, whereby singlet oxygen generation by particles comprised of silicon phthalocyanine has been used to generate a delayed luminescence. The delayed luminescence is proportional to the analyte concentration (*Clin. Chem.* 42:1518-1526).

The teachings herein show that light (ambient or focused) decreased the effectiveness in binding reactions of antibodies, peptide and ligand analogue fluorescent conjugates. The mechanism for the decrease in effectiveness is believed to be related to the generation of reactive species, such as singlet oxygen or radicals, by the fluorescent molecules. The inactivation of biological reagents in fluorescent conjugates makes them unreliable for use in assays. The inactivation of antibody binding in immunoassays or of nucleic acid hybridization in nucleic acid assays is generally manifest by a decrease in the slope of a dose response curve of the assay.

As disclosed herein, light-mediated inactivation of biological reagents in fluorescent conjugates is very dramatic. It has been found that the degradation of biological reagents in fluorescent conjugates is independent of the fluorescent molecule used in making the fluorescent conjugate. The efficiency of the inactivation is believed to be a result of two factors: First, the high local concentrations of both the dye and the biological reagent; and, second, the relative proximity of the biological reagent and the fluorescent dye in the fluorescent conjugates.

The presumed mode of degradation is type I and/or type II mechanisms of phototoxicity. In the case of type I mechanisms, the triplet sensitizer, that is, the triplet state of a fluorescent dye, reacts with nearby molecules through an electron or hydrogen transfer process. Free radicals are thus formed; namely the semireduced sensitizer and the semioxidized substrate. The semireduced sensitizer can react with oxygen to form a superoxide radical anion, which can further react with other molecules. The semioxidized sensitizer can become reduced by another molecule to form a semioxidized substrate, which can further react.

In the case of type II mechanisms, the triplet sensitizer can react with ground state oxygen to form singlet oxygen which can further react with other molecules, such as biomolecules and reagents to give oxidized products. (See, e.g., *Int. J. Radiat. Biol.* (1995) 67:85-91).

As disclosed herein, biological reagents associated with fluorescent dyes become inactivated or ineffective through the triplet state of the dye. The generation of triplet states of fluorescent dyes can result in the formation of a variety of radical species, including but not limited to singlet oxygen, superoxide radicals, hydroxyl radicals and organic radicals. These radical species have been known to cause damage to biological cells and proteins. Accordingly, these reactive triplet state species react with the surface of the biological reagent. Consequently, there will be a decreased effectiveness of an antibody for binding to analyte, or for a peptide or ligand analogue for binding to antibody. The inventive teachings set forth compositions which slow or prevent the light-induced destruction of biological reagents.

Stabilization of Biological Reagents

This invention relates to the stabilization of biological reagents conjugated to fluorescent particles or conjugated to a fluorescent molecule, as well to the preparation of such conjugates. The biological reagent can comprise a protein, peptide, ligand analogue or nucleic acid component. When a biological reagent is stabilized in accordance with the invention, phototoxic degradation of the biological reagent in a fluorescent conjugate is impeded.

Accordingly, it has now been found that inactivation of biological reagents conjugated to fluorescent molecules or fluorescent particles can be decreased or prevented by use of radical scavengers termed quenchers, oxygen depleting systems in solutions that contain the fluorescent biological reagent conjugates, chemical linkages in conjugates to minimize the effects of radicals, or combinations thereof.

Another embodiment of this invention comprises a system which consumes dissolved oxygen. For example, a system of this embodiment comprises catalyse, glucose oxidase, and glucose, as discussed in greater detail herein.

In a preferred embodiment, solutions containing chemically oxidizable compounds that are associated with or conjugated to fluorescent molecules, also contain singlet oxygen and/or free radical quenchers to minimize or prevent oxidation of the chemical species. Oxidizable compounds include those that are capable of being converted from one oxidation state to a higher one. In general, most oxidations involve a gain of oxygen and/or a loss of hydrogen.

In another preferred embodiment, solutions containing biological reagents that are associated with or conjugated to fluorescent molecules, also contain singlet oxygen and/or free radical quenchers to minimize or prevent inactivation of the biological reagent. Biological reagents include, peptides and proteins containing oxidizable amino acids or pendant molecules, and nucleic acids.

In another preferred embodiment, solutions containing antibodies that are associated with or conjugated to fluorescent molecules or particles also contain singlet oxygen and/or free radical quenchers to minimize or prevent the ability of the antibody to bind its antigen. Antibodies include, polyclonal and monoclonal antibodies and binding fragments generated by recombinant protein synthesis or other techniques.

In yet another preferred embodiment, solutions containing nucleic acids that are associated with or conjugated to fluorescent molecules, also contain singlet oxygen and/or free radical quenchers to minimize or prevent the inactivation or slow the rate of hybridization of the nucleic acid to a complementary nucleic acid strand.

Compounds that can be utilized as quenchers of singlet oxygen include, but are not limited to those listed in Table 1. Compounds that can be utilized as quenchers of free radicals include, but are not limited to, those listed in Table 2.

TABLE 1

Singlet Oxygen Quenchers carotenoids: naturally occurring and synthetic
tocopherols and tocopheramines: homologues, isomers, derivatives and related compounds
thiols: e.g. glutathione, ergothionine, cysteine, N acetyl-cysteine, dihydrolipoic acid, thiol-containing proteins and peptides)
amino acids: tryptophan, tyrosine, histidine, methethione, cysteine, and peptides and proteins containing these amino acids
probucol
2,2,6,6-tetra-methyl-piperidine (TEMP)
plamitoyl ascorbic acid
caffeine
squalene
esters of polyunsaturated fatty acids
flavonoids
lidocaine
imidazole and derivatives
phthalocyanines and naphthalocyanines TABLE 1-continued Singlet Oxygen Quenchers p-aminobenzoic acid (PABA)
curcumin
spermine
spermidine
merocyanine 540
cholesterol
azide

TABLE 2

Free Radical Quenchers

Metal Complexes manganese (II) stearate
manganese (II) acetate
bis-(acetylacetonate)manganese (II)
N,N'-ethylene-bis-(salicylideneiminato)manganese (II)
bis-(dimethylglioximato)-bis-pyridineferrous
ferric stearate
tris-(acetylacetonato) ferric
bis-(dimethylglioximato)ammineiodidecobalt (II)
bis-(dimethylglioximato)amminechloridecobalt (II)
tris-(dimethylglioximato)cobalt (II)
bis-(dimethylglioximato)ammineiodidecobalt (II)
bis-(dimethylglioximato)pyridineiodidecobalt (II)
bis-(dimethylglioximato)pyridinechloridecobalt (II)
bis-(dimethylglioximate)-bis-pyridinecobalt (II)
cobalt (II) stearate
cobalt (II) chloride
cobalt (II) acetate
cobalt (II) cyclohexylcarboxylate
bis-(acetylacetonato)cobalt (II)
N,N'-ethylene-bis-(salicylideneiminato)cobalt (II)
porfirine cobalt (II)
bis-(salicylate) nickel
N,N'-ethylene-bis-(salicylideneiminato)nickel
N,N'-ethylene-bis-(N-p-toluidinyl)salicylideneiminato)nickel
copper stearate
bis-(dimethyiglioximato)copper
bis-(salicylate)copper
bis-(dimethyiglioximato)copper
bis-(diphenyiglioximato)copper
bis-(dimethyiglioximato)ammineiodidecopper
copper sulfate
copper acetate
bis-(acetylacetonato)copper
porfirine copper Phenols hydroxybenzenes
benzoquinons
catechol and derivatives
cresol isomers (o-, m-, p-)
chromans
dihydrobenzofurans
1,2-ethane-2,2'-bis-(4,6-di-tert-butyphenol)
hydroxyfluorenes
hydroquinone
4,4'-methane-bis-(2,6-di-tert-butylphenol)
dihydroxynaphthalene
naphthol isomers
pentaerithritol ester of 3,5-di-tert-butyl-4-hydroxyphenylproprionic acid
hydroxyphenantrene isomers
phenol and derivatives
pentaeritrityl tetrakis[3-(3,5-di-tert-butyl-4-hydroxyphenyl)proprionate]
ethyleneglycol bis-(3,5-di-tert-butyl-4-hydroxyphenyl)propionate
resorcinol
silane, tetra(ethyloxy-3,5-di-tert-butyl-4-hydroxyphenyl)
4,4'-sulfide-bis-(3,5-di-tert-butyl-4-dydroxybenzyl)
2,2'-sulfide-bis-[4-methyl-5-hydroxy-6-(1'-phenyl)ethyl]

TABLE 2-continued

Free Radical Quenchers 2,2'-disultide-bis-[4-methyl-6-hydroxy-5-(1'-phenyl)ethyl]
indophenol
tetrahydroquinoline, 5,7,8-trimethyl-6-hydroxy-N-acetamido
tetrahydroquinoline, 5,7,8-trimethyl-6-hydroxy-N-ethyl
tocol, 5,7-dimethyl
tocopherol isomers ($\alpha$, $\beta$, $\gamma$, $\delta$)
Aromatic Amines carbasol
mono- and di-naphthylamines
diphenylamine and derivatives
p-phenylendiamine derivatives
phenylamine
phenylnaphthylamine isomers
4-phenyloxyphenyl-2-naphthylamine
4-(spirotetrahydrofuran-2')spirocyclohexyl-1,2,3,4-tetrahydroquinoline
4-tert-butylphenyl-1-(4-tert-butyl)naphthylamine
1,2,3,4-tetrahydroquinoline, 2,2,4-trimethyl
Hydroxylamines And Nitroxyl Radicals 9-azabicyclo[3.3.1]nonanehydroxylamine
8-azabicyclo[3.2.1]octanehydroxylamine
1,4-diazacycloheptane, 2,2,6,6-tetramethyl-5-oxo
2,5-dihydroimidazole derivatives
2,5-dihydropyrrol derivatives
3,4-dihydropyrrol derivatives
1,2-dihydroquinoline derivatives
hydroxylamine derivatives
piperidine derivatives
pyrrolidine derivatives
tetrahydroimidazole derivatives
tetrahydropyridine derivatives
tetrahydropyrrol derivatives
tetrahydroquinoline derivatives
Thiophenols thionaphthol isomers
thiophenol and derivatives
phenolsuifides
Phosphorous And Sulfur Containing Antioxidants phosphines
phosphites
suifides
disulfides
sulfoxides
metalthiocarbamates
metalthiophosphates
Biological Antioxidants Low Molecular Weight, Water Soluble ascorbate;
thiols;
urate;
bilirubin and biliverdin;
flavins (e.g., vitamin B2);
quercetin
Low Molecular Weight, Lipid Soluble carotenoids (natural and synthetic) and related polyenes;
vitamin A (i.e. retinol, retinal, retinoic acid) and
related compounds;
tocopherol homologues, isomers, derivatives and related
compounds;
ubiquinol and ubiquinone;
flavonoids
Proteins thiol containing: albumin; thioredoxin; glutaredoxin
redox active: cytochrome c; myoglobin
enzymes: superoxide dismutase (SOD), catalase, various
peroxidases
Drugs salicylate; ebselen; synthetic thiols and thiol
derivatives; probucol and its derivatives;

TABLE 2-continued

Free Radical Quenchers phenylbutylnitrone; spin traps; nitecapone and its
analogs; penicillamine; lazaroids; aminosalicylates;
stobadine; nitroxides; tamoxifen and estrogens;
plasmalogens; calcium channel blocking drugs; nitroxides;
melatonin A further aspect of the invention comprises use of heterofunctional reagents, such as heterobifunctional reagents, which have long molecular distances. The linkages produced thereby were used in fluorescent conjugates to associate a fluorescent molecule with a biological reagent. Accordingly, the biological reagent was at a maximized distance from the source of radical production. Maximizing the distance of the biological reagent from the source of the radical producer increased the time that the radical must travel, and therefore increased the decay of the radical before it reached and then damaged the biological reagent. Such cross-linking reagents include but are not limited to: heterofunctional PEGs comprised of N-hydroxysuccinidyl (NHS) esters of poly (oxyethylene) derivatives containing a maleimide or vinyl sulfone group or similar electrophilic moiety; long chain forms of succinimidyl-4-(N-maleimidomethyl)cyclohexane-1-carboxylate (SMCC), such as succinimidyl-4-(N-maleimidomethyl)cyclohexane-1-carboxy-(6-amido-caproate), or of succinimidyl 3-(2-pyridyldithio) propionate (SPDP), such as succinimidyl-6-[3-(2-pyridyldithio) propionamido] hexanoate; and heterofunctional peptide derivatives.

An alternative embodiment of this invention utilized a protein substrate which was juxtaposed between a fluorescent molecule and a biological reagent. The protein substrate functioned to interact with the reactive species, such that the reactive species was quenched before it moved into the sphere of the biological reagent involved in that assay. This led to increased stability of the assay reagents over time. An example of this embodiment is set forth as Example 7.

Another embodiment of this invention incorporated water insoluble quenchers into a fluorescent particle conjugate. Such quenchers include but are not limited to quenchers of singlet oxygen, free radicals and excited triplet states; examples of these are given in Tables 1 and 2. A preferred quencher is the carotenoid $\beta$-carotene, which can quench singlet oxygen, free radicals and excited triplet states; most other quenchers listed in Tables 1 and 2 possess the identified quenching activities. The water insoluble quenchers in physical contact with the dye molecules interacted efficiently with the reactive species, because they were closer to the source of production of the reactive species than the biological reagent involved in the assay. An example of this embodiment is set forth as Example 8.

Another embodiment of this invention comprised a combining water soluble quenchers and emulsions of water insoluble quenchers, including but not limited to detergent micelles and liposomes, with a solution that contained the fluorescent conjugate or fluorescent particle conjugate. Examples of this embodiment are set forth as Examples 5 and 6.

Another embodiment of this invention comprised a combination of water insoluble quenchers incorporated into a fluorescent particle conjugated to a biological reagent, in combination with a system which consumes dissolved oxygen present in the solution that contains the conjugate.

Another embodiment of this invention comprised a combination of water soluble quenchers or emulsions of water insoluble quenchers in combination with a system which consumes dissolved oxygen in a solution that contains a fluorescent conjugate.

Another embodiment of this invention comprises a combination of both water insoluble quenchers incorporated into the fluorescent conjugate particle, water soluble quenchers or emulsions of water insoluble quenchers in the solution that contains the conjugate, together with a system which consumes dissolved oxygen in the solution that contains the fluorescent conjugate.

EXAMPLES

Example 1

Effect of Light Exposure on the Activity of Antibodies Coupled to Fluorescent Particles Particles coupled with anti-troponin antibodies (this and all other antibody conjugates used in this and the following examples as well as the particular fluorescent molecules involved were disclosed, and were prepared as disclosed, in U.S. patent application Ser. Nos.: 08/409,298 and 08/409,825, each filed 23 Mar. 1995; and U.S. patent application Ser. No.: 08/620,597 filed 22 Mar. 1996. U.S. patent application Ser. Nos.: 08/409,298; 08/409,825; and 08/620,597, including all respective parent applications are fully incorporated by reference herein) were diluted to 0.14% solids in air-saturated storage buffer (hereafter called storage buffer, which had the following composition: STABILCOAT® (an aqueous solution containing purified bovine protein and other non-toxic chemicals in phosphate buffered saline, pH 7.0-7.4) (BSI, Eden Prairie, Minn.), 13% (vol/vol); sucrose, 23 mg/mL; bovine serum albumin (30% solution, manufacturing grade, Bayer Corp. Kankakee, Ill.), 13 mg/mL; potassium phosphate, 30 mM; potassium borate, 6 mM; sodium chloride, 90 mM; pH 7.5)) to form an incubation mixture and then split among two colorless 1.5 mL microcentrifuge tubes, one of which was incubated under room light (light provided by standard white fluorescent tubes), and the other protected from light, both at room temperature.

Antibody activity was determined by immunoassay by combining an aliquot of the incubation mixture containing antibody conjugates with an equal volume of troponin assay reagent (this reagent consisted of 6 ng/mL human cardiac troponin I (Biotech International, Inc., Seattle, Wash.) and 2 µg/mL biotinylated goat anti-troponin I peptide 3 specific antibody (BioPacific, Emeryville, Calif.), which formed a complimentary pair with the anti-troponin antibodies coupled to the fluorescent particles (i.e., a fluorescent conjugate), in assay reagent buffer consisting of 140 mM sodium chloride, 10 mM potassium phosphate, 40 g/L bovine serum albumin (30% solution, manufacturing grade, Bayer Corp., Kankakee, Ill.), pH 7.4); the resulting sample was incubated for 15 min and then assayed in an immunoassay device as disclosed in U.S. patent application Ser. No. 08/423,582 (filed Apr. 18, 1995).

Briefly, the sample was loaded at the top of the diagnostic lane of the device and allowed to flow by capillary action through the diagnostic lane that had avidin-HS bound on one surface in a capture zone. After the sample flowed into the device, assay reagent buffer was loaded at the top of the diagnostic lane to wash away unbound reagents from the capture zone. The amount of antibody conjugate bound to the capture zone was quantified by scanning the diagnostic lane with a fluorometer consisting of a laser diode excitation source (670 nm) and a silicon photodiode detector measuring fluorescence at the wavelength maximum of 760 nm with the appropriate optical filters and electronics to obtain the fluorescence signal. A unit of antibody activity was defined based on the slope of the dose response curve of the assay. Assay activities in Table 3 are expressed relative to the activity of the sample that had not been exposed to light (i.e., the dark control), which was set at 100%.

TABLE 3

| time of light exposure | % of dark control |
|---|---|
| 0 hours | 100 |
| 14 hours | 25 |
| 24 hours | 16 |

These results showed that exposure of the antibody conjugates to light resulted in a time dependent loss of assay signal when compared to a dark control.

Example 2

Effect of Particle Dye Content on the Light Induced Inactivation of Antibodies Coupled to Fluorescent Particles Antibody conjugates with both anti-troponin and anti-CKMB antibodies were prepared with latex particles containing fluorescent dye at three different concentration levels. The three particle preparations were diluted to 0.14% solids in argon-purged storage buffer containing 5 mM sodium ascorbate and the glucose oxidase system (10 mg/mL glucose, 10 µg/mL glucose oxidase (Calbiochem, San Diego) and 10 µg/mL catalase (Calbiochem, San Diego)) and then split among two colorless 1.5 mL microcentrifuge tubes, one of which was incubated under room light, and the other protected from light.

After 24 hours, the incubation mixtures were assayed for activity by immunoassay by combining aliquots of each with an equal volume of troponin/CKMB assay reagent (this reagent consisted of 20 ng/mL each human cardiac troponin I (Biotech International, Inc., Seattle, Wash.) and CKMB (Genzyme, San Carlos, Calif.)), 2 µg/mL biotinylated goat anti-troponin I peptide 3 specific antibody (BioPacific, Emeryville, Calif.) and 2 µg/mL fluorescein-labeled anti-CKMB antibody (IIL-3, IIL Inc.), which formed a complimentary pair with the anti-CKMB antibodies coupled to the fluorescent particles, in buffer containing 140 mM sodium chloride, 10 mM potassium phosphate, 40 g/L bovine serum albumin (30% solution, manufacturing grade, Bayer Corp., Kankakee, Ill.), pH 7.4), incubating for 2 min, and assaying the incubation mixture as described in Example 1. The devices employed in this example had capture zones comprised of immobilized anti-fluorescein antibody and avidin-HS. In Table 4, assay activities are expressed relative to the activity of the samples that had not been exposed to light (i.e., the dark control), which was set at 100%.

TABLE 4

| relative dye content of particle | % of dark control | |
|---|---|---|
| | troponin assay | CKMB assay |
| 1 | 48 | 30 |
| 3 | 22 | 19 |
| 9 | 11 | 13 |

These results showed a direct, positive correlation between the dye content of the antibody conjugates and the degree of light dependent inactivation of antibodies coupled to the particle. This was seen in both the troponin and CKMB antibody assays.

Example 3

Effect of Green Light on the Activity of Antibodies Coupled to Fluorescent Particles An incubation mixture of anti-troponin conjugates was prepared as described in Example 1 and was divided among three colorless 1.5 mL centrifuge tubes, which were incubated respectively under green fluorescent light (Model F40G, General Electric), standard white fluorescent light or in the dark. After 24 hours, each incubation mixture was sampled and assayed as described in Example 1, the results are set forth in Table 5.

TABLE 5

| ambient light source | assay activity (Units) |
|---|---|
| dark (control) | 20 |
| white fluorescent tube | 4 |
| green fluorescent tube | 26 |

These results showed that light emitted by green fluorescent tubes did not exert the same deleterious effect on antibody activity as seen with full spectrum white light. The excitation wavelength maximum of the fluorescent dye in the antibody conjugate is 670 nm, which corresponds to the red region of the visible spectrum. The emission spectrum of the green fluorescent light contains much less red light than that of the white fluorescent light; thus, production of fluorescence was impeded during preparation of the fluorescent conjugates.

Example 4

Effect of Dissolved Oxygen Deprivation on the Light Induced Inactivation of Antibodies Coupled to Fluorescent Particles Particles coupled with anti-troponin I antibody were diluted to 0.14% solids in air-saturated storage buffer, in argon-purged storage buffer and in argon-purged storage buffer prepared with 100 mM sodium ascorbate, and were incubated in colorless 1.5 mL microcentrifuge tubes under room light. Samples were withdrawn from the incubation mixtures and were assayed as described in Example 1. The antibody activity of the conjugates in air-saturated storage buffer was 74, 19 and 12 Units after 0, 14 and 24 hours of exposure to light, respectively. In Table 6, antibody activity at each time point is expressed relative to the activity of the conjugates kept in air-saturated storage buffer.

TABLE 6

| time of light exposure | storage buffer | relative activity |
|---|---|---|
| 14 hours | air-saturated | 1.0 |
| | argon-purged | 2.5 |
| | 100 mM ascorbate, argon-purged | 2.5 |
| 24 hours | air-saturated | 1.0 |
| | argon-purged | 2.9 |
| | 100 mM ascorbate, argon-purged | 4.4 |

These results showed that decreasing the level of dissolved oxygen in the incubation mixtures, either by purging the mixture with an inert gas or by including a autoxidizable compound in the mixture, protected the antibody conjugate against light induced inactivation. An advantage of including an antioxidant, such as ascorbate, is particularly evidenced at the longer time point, where ascorbate afforded a greater degree of protection than simply purging the mixture with argon.

Example 5

Effect of Antioxidants on the Light Induced Inactivation of Antibodies Coupled to Fluorescent Particles Particles coupled with anti-troponin I antibody were diluted to 0.14% solids in air-saturated storage buffer and in argon-purged storage buffer prepared with 20 mM ascorbate and the glucose oxidase system as described in Example 2. Each incubation mixture was divided among two colorless 1.5 mL microcentrifuge tubes, one of which was incubated under room light, and the other protected from light. After 17 hours the mixtures were assayed for activity by immunoassay by combining aliquots of each with an equal volume of troponin assay reagent, incubating 2 min, and assaying as described in Example 1. The results are set forth in Table 7.

TABLE 7

| antioxidants | incubation condition | assay activity (Units) |
|---|---|---|
| none | in dark | 41 |
| | under room light | 6 |
| ascorbate, glucose oxidase system | in dark | 36 |
| | under room light | 35 |

These results showed that the addition of an antioxidant and an oxygen consumption system to the storage buffer greatly enhanced the stability of the antibody conjugate to light exposure; here it can be seen that the activity of conjugates incubated in the absence of antioxidants decreased by 85%, whereas conjugates incubated in the presence of an antioxidant and the oxygen consuming system retained their activity.

Example 6

Conditions for Stabilizing Antibody Conjugates

Particles coupled with anti-troponin I antibody were diluted to 0.14% solids in argon-purged storage buffer prepared with final concentrations of 50 mM sodium ascorbate, 20 mM TROLOX® (6-Hydroxy-2,5,7,8-tetramethylchroman-2-carboxylic Acid) (Aldrich Chemical Co., Milwaukee, Wis.), 10 mM sodium azide, and 10 mg/mL glucose. The incubation mixture was contained in two clear, colorless glass vials. Glucose oxidase was added to the mixtures and the vials were argon purged. The vials were then sealed with a septum lined crimp cap. One of the vials was wrapped in foil to exclude light, while the other was left exposed to light. Both vials were placed in a 3-neck round bottom flask, to which a nitrogen gas line, an exhaust line leading to a bubble chamber, and a stopper were attached. The flask was kept under room light and a continuous flow of nitrogen for 3.8 days. Antibody activity was determined as described in Example 1. Results are set forth in Table 8.

TABLE 8

| incubation condition | assay activity (Units) |
|---|---|
| in dark | 25 |
| under room light | 25 |

These results demonstrated that minimizing or eliminating oxygen from antibody conjugates can prevent the light induced inactivation.

In an additional experiment it was found that samples which were prepared with the glucose oxidase system but without the antioxidants ascorbate, Trolox and azide, and kept under an atmosphere of nitrogen, retained full activity during exposure to light for 7.8 days.

Example 7

Effect of an Intervening Protein Coat on the Light Induced Inactivation of Antibody Conjugates Particles coupled with anti-troponin I antibody were prepared from latex particles that had been adsorbed with bovine serum albumin prior to antibody coupling, and from latex beads that had not received the bovine serum albumin. The bovine serum albumin was adsorbed to fluorescent particles at 5 mg/mL protein and 0.5% solids. The unbound protein was separated using gel filtration chromatography. The antibody was coupled to the protein coat with SMCC and SPDP (Pierce Chemical Co., Rockford, Ill.) using standard protein coupling procedures.

Mixtures at 0.14% solids of both of these particles were prepared by diluting them into air-saturated storage buffer and then split among two colorless 1.5 mL microcentrifuge tubes. A tube from each set was incubated under room light and in the dark. After 17 hours samples were withdrawn from each tube and assayed as described in Example 1. Results are set forth in Table 9.

TABLE 9

| protein coat | storage condition | % of dark control |
|---|---|---|
| none | in dark (control) | 2.9 |
| | under room light | 2.9 |
| albumin | in dark (control) | 100 |
| | under room light | 17 |

These results showed that particles prepared with an intervening layer of protein were more resistant to light induced antibody inactivation than particles lacking a protein layer. Other protein coats, which were comprised of fibrinogen, cytochrome C and thyroglobulin, also reduced the light induced inactivation of the antibody conjugates (data not shown).

Example 8

Affect of Water Insoluble Antioxidants Incorporated into the Particle on the Light Induced Inactivation of Antibodies Coupled to Fluorescent Particles Particles coupled with anti-troponin I antibody were prepared from latex particles that contained the carotenoid lycopene (Sigma Chemical Co., St. Louis, Mo.) in addition to the fluorescent dye, a separate set of coupled particles was prepared from latex beads that contained the fluorescent dye but no lycopene. Each of the particle preparations was diluted to 0.14% solids in air-saturated storage buffer and then split among two colorless 1.5 mL microcentrifuge tubes. One tube from each set was incubated under room light and the other was shielded from light.

After 22 hours samples were withdrawn from each tube and assayed as described in Example 1. Assay activities are expressed relative to the activity of the sample that had not been exposed to light. The results are set forth in Table 10.

TABLE 10

| antioxidant | incubation condition | % of dark control |
|---|---|---|
| none | in dark (control) | 100 |
| lycopene | in dark (control) | 100 |
| | under room light | 84 |

These results showed that incorporating an antioxidant such as lycopene into the fluorescent particle decreased the degree of light induced inactivation of the antibody coupled to the particle. Particles prepared with other carotenoids (e.g. lutein, β-carotene, bixin, crocetin and physalien) and antioxidants (e.g. nickle complexes, stilbene and BHA) were also tested and found to be more resistant to light induced inactivation than control particles without these protectors (data not shown).

Example 9

Effect of Antioxidants on the Light Induced Inactivation of Antibodies Coupled to Different Fluorescent Particles Particles coupled with anti-CKMB antibody were prepared from fluorescent latexes obtained commercially (Molecular Probes, Inc., catalog numbers L7189, L7201 and L7204) and from a different standard fluorescent latex prepared for this and the other experiments herein. Mixtures at 0.14% solids of these particles were prepared by diluting them either into air-saturated storage buffer or into argon-purged storage buffer containing 5 mM sodium ascorbate, 10 mM Trolox, 10 mM sodium azide, 10 mg/mL glucose and 10 µg/mL each catalase and glucose oxidase. Each mixture was split among two clear, colorless glass vials and the vials were sealed with septum lined crimp caps. Vials containing the antioxidant mixtures were evacuated with argon prior to the addition of the glucose oxidase and capping. All vials were placed in a 3-neck round bottom flask, to which a nitrogen gas line, an exhaust line leading to a bubble chamber, and a stopper were attached. The flask was evacuated with nitrogen, sealed and placed under room light. After a 4 day incubation, samples were withdrawn from the vials and assayed for antibody activity immunoassay.

Immunoassays were conducted by combining the samples with an equal volume of CKMB assay reagent (this reagent consisted of 50 ng/mL CKMB (Genzyme, San Carlos, Calif.) and 2 µg/mL of a biotinylated anti-CKMB antibody, which formed a complimentary pair with the antibodies coupled to the fluorescent particles, in buffer containing 140 mM sodium chloride, 10 mM potassium phosphate, 40 g/L bovine serum (30% solution, manufacturing grade, Bayer Corp., Kankakee, Ill., pH 7.4), incubating the reaction mixture for 15 min, and then analyzing it by device assay as described in Examples 1 and 2.

Assay signals were determined using a fluorescence spectrometer (model LS50B, Perkin Elmer, Norwalk, Conn.) and are expressed as relative fluorescence. Results are set forth in Table 11.

TABLE 11

| | anti-CKMB fluorescent particle | | | |
|---|---|---|---|---|
| | spectral maxima (nm) | | | assay activity |
| latex | excitation | emission | storage buffer | (rel. fluor./ng/mL) |
| Molecular Probes L7204 | 488 | 685 | without antioxidants | 0.10 |
| | | | with antioxidants | 0.38 |
| Molecular Probes L7201 | 543 | 620 | without antioxidants | <0.01 |
| | | | with antioxidants | 0.40 |
| Molecular Probes L7189 | 633 | 720 | without antioxidants | 0.03 |
| | | | with antioxidants | 0.22 |
| Prepared latex | 670 | 760 | without antioxidants | <0.01 |
| | | | with antioxidants | 0.19 |

These results showed that antibody conjugates prepared with a variety of fluorescent dyes were all susceptible to light induced antibody inactivation. It was also seen that, in each case, the inactivation could be decreased by including antioxidants in the storage buffer and minimizing exposure to dissolved oxygen.

Example 10

Effect of Light and Antioxidants on the Assay Response of an Antibody Conjugate and a Morphine Conjugate Florescent particles coupled with anti-dansyl antibodies (antibody conjugate) or morphine (morphine conjugate; i.e., a ligand analog conjugate) were tested with antioxidants in an immunoassay.

The assay reagents were incubated either in an essentially dark location (under dim green lights) or under white room light. The reagents included the antibody conjugate, an anti-morphine antibody that was coupled with a peptide tag, the morphine conjugate and either no antioxidants or the antioxidants ascorbate (200 mM after reconstitution) and TROLOX® (6-Hydroxy-2,5,7,8-tetramethylchroman-2-carboxylic Acid) (10 mM after reconstitution). The immunoassay was performed essentially as described in Example 1. The capture zones on the device were comprised of anti-peptide antibody to bind the ligand analogue conjugate and a dansyl derivative to bind the antibody conjugate.

The fluorescent signals from the assays run under white light were divided by the fluorescent signals from the assays ran in the dark, to obtain the assay response set forth in Table 12. The results showed that maximum assay response for devices run under white light was obtained only with the antioxidants ascorbate and TROLOX® (6-Hydroxy-2,5,7,8-tetramethylchroman-2-carboxylic Acid).

In separate experiments, TROLOX® (6-Hydroxy-2,5,7,8-tetramethylchroman-2-carboxylic Acid) alone and ascorbate alone also protected the light induced inactivation (data not shown).

TABLE 12

| | % of Maximum Assay Response | |
|---|---|---|
| Antioxidant(s) | Antibody Conjugate | Morphine Conjugate |
| None | 69% | 71% |
| Ascorbate and Trolox | 100% | 100% |

Example 11

Use of Heterobifunctional Reagents to Increase the Diffusion Distance for Reactive Species in Conjugates Heterobifunctional reagents which have long molecular distances were used to prepare fluorescent conjugates. The linkages produced thereby were used to associate a fluorescent molecule with a biological reagent. Such cross-linking reagents include but are not limited to: heterofunctional PEGs comprised of N-hydroxysuccinidyl (NHS) esters of poly (oxyethylene) derivatives containing a maleimide or vinyl sulfone group or similar electrophilic moiety; a heterofunctional crosslinking reagent such as a sulfhydryl and amino reactive heterobifunctional crosslinking reagent; and, heterofunctional peptide derivatives. In preferred embodiments, the sulfhydryl and amino reactive heterobifunctional crosslinking reagent can comprise long chain forms of SMCC or SPDP; e.g., succinimidyl-4-(N-maleimidomethyl)cyclohexane-1-carboxy-(6-amido-caproate) and succinimidyl-6-[3-(2-pyridyldithio)propionamido] hexanoate, respectively. It being understood that other linking agents known in the art can be used in accordance with the invention disclosed and claimed herein.

Accordingly, the biological reagent in a conjugate was at a maximized distance from the source of radical production at the signal moiety. Maximizing the distance of the biological reagent from the source of the radical production increased the time that the radical must travel, and therefore increased the decay of the radical before it reached and then degraded or damaged the biological reagent. Preferred embodiments of the invention comprise conjugates comprising long molecular distances between biological reagent and fluorescent signal moieties, in combination with other inventive embodiments to stabilize the fluorescent conjugates such as an oxygen depleting system, a protein, an antioxidant, or a combination thereof.

Closing

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention pertains. Although any methods and materials similar to equivalent to those described herein can be used in the practice or testing of the invention, the preferred methods and materials are now described. All publications mentioned herein are incorporated fully by reference herein.

The invention claimed is:

1. A fluorescent composition for use in an assay for an analyte of interest, comprising:
   a particle;
   one or more fluorescent molecules bound to the surface of or within said particle;
   a biological reagent selected from the group consisting of a receptor for said analyte of interest and a ligand analogue that competes with said analyte of interest for binding to a receptor, said biological reagent directly or indirectly bound to said particle, wherein said biological reagent is selected from the group consisting of an antibody, a nucleic acid, a protein, and a peptide; and
   one or more protective agents comprising an antioxidant within said particle, said protective agent(s) configured and arranged to protect said biological reagent from inactivation when said particle is exposed to light and oxygen.

2. A fluorescent composition according to claim 1, wherein said particle is a latex particle.

3. A fluorescent composition according to claim 1, wherein said particle is a liposome.

4. A fluorescent composition according to claim 1, wherein said particle is an alumina particle.

5. A fluorescent composition according to claim 1, wherein said particle is a silica particle.

6. A fluorescent composition according to claim 1, wherein said particle comprises one or more fluorescent molecules within said particle.

7. A fluorescent composition according to claim 6, wherein said protective agent(s) comprise a protein adsorbed to the surface of said particle.

8. A fluorescent composition according to claim 7, wherein said biological reagent is indirectly bound to said particle through said protein.

9. A fluorescent composition according to claim 1, wherein said biological reagent is directly bound to said particle.

10. A fluorescent composition according to claim 1, wherein said antioxidant is selected from the group consisting of lycopene, lutein, β-carotene, bixin, corcetin, physalien, nickel complex, stilbene, and BHA.

11. A fluorescent composition according to claim 1, wherein said protective agent(s) comprise a protein adsorbed to the surface of said particle.

12. A fluorescent composition according to claim 11, wherein said biological reagent is indirectly bound to said particle through said protein.

13. A fluorescent composition according to claim 6, wherein said protective agent(s) comprise a heterofunctional crosslinking reagent between said biological reagent and said particle, said heterofunctional crosslinking reagent having a length sufficient to protect said biological reagent from inactivation when said particle is exposed to light and oxygen.

14. A fluorescent composition according to claim 13, wherein said heterofunctional crosslinking reagent is selected from the group consisting of succinimidyl-4-(N-maleirni-domethyl)-cyclohexane-1-carboxy-(6-amido-caproate) and succinimidyl-6-[3-(2-pyridyldithio)propionarnido]hexanoate.

15. A fluorescent composition according to claim 1, wherein said fluorescent composition is suspended in an aqueous solvent.

16. A fluorescent composition according to claim 15, wherein said aqueous solvent comprises an antioxidant.

17. A fluorescent composition according to claim 15, wherein said aqueous solvent comprises an oxygen depleting system.

* * * * *

UNITED STATES PATENT AND TRADEMARK OFFICE
CERTIFICATE OF CORRECTION

| | | |
|---|---|---|
| PATENT NO. | : 7,588,908 B2 | Page 1 of 1 |
| APPLICATION NO. | : 10/338182 | |
| DATED | : September 15, 2009 | |
| INVENTOR(S) | : Kenneth F. Buechler et al. | |

It is certified that error appears in the above-identified patent and that said Letters Patent is hereby corrected as shown below:

On the Title page, under the Related U.S. Application Data, item (63) is missing. Please add: Continuation of application No. 08/837,309, filed on April 9, 1997, now Pat. No. 6,544,797.

On claim 3, please correct a misspelled word... "liposorne" should be "liposome".

Signed and Sealed this

Twenty-first Day of December, 2010

David J. Kappos
*Director of the United States Patent and Trademark Office*